United States Patent [19]

Kodadek et al.

[11] Patent Number: 5,563,263

[45] Date of Patent: Oct. 8, 1996

[54] $D_4$-SYMMETRIC PORPHYRIN-BASED CATALYSTS, PROCESSES FOR PREPARING SAME, AND PROCESSES FOR USING SAME

[75] Inventors: Thomas J. Kodadek; John F. Barry, both of Austin, Tex.

[73] Assignee: Hoechst Celanese Corporation, Somerville, N.J.

[21] Appl. No.: 306,804

[22] Filed: Sep. 14, 1994

[51] Int. Cl.[6] .......................... C07D 487/22; C07C 29/50
[52] U.S. Cl. .............................................. 540/145; 568/910
[58] Field of Search ................................................ 540/145

[56]         References Cited

U.S. PATENT DOCUMENTS 5,480,986   1/1996  Lyons et al. ............................ 540/145

OTHER PUBLICATIONS

Halterman et al. J. Org. Chem., 56, pp. 5253–5254 1991.
Cense et al. Chem. Abstr. vol. 92: 215411v 1980.
Chem. Comm. 1984, p. 207.

*Primary Examiner*—Mukund J. Shah
*Assistant Examiner*—Pavanaram K. Sripada
*Attorney, Agent, or Firm*—James J. Mullen; Donald R. Cassady

[57]         ABSTRACT

The present invention provides novel $D_4$-symmetric chiral porphyrins derived from 1R-(+)-nopinone. The simplicity and flexibility of this synthetic protocol provides an attractive route to this novel class of porphyrins starting from cyclic ketones. For example, the chloromanganese (III) derivatives of the new macrocycles have utility as catalysts for the asymmetric epoxidation of aromatic alkenes.

15 Claims, 4 Drawing Sheets where  M  is Mn, Fe, Al, Rh, Ni, Co, Ru, or Cu:
       Ar  is the same arenyl group as shown on the left and right sides of the main structure; and
       X  is Cl, Br, F, I, $BF_4$, or $PF_6$

D₄-SYMMETRIC PORPHYRIN-BASED CATALYSTS, PROCESSES FOR PREPARING SAME, AND PROCESSES FOR USING SAME

BACKGROUND OF THE INVENTION

1. Field of the Invention

The present invention is directed to a new class of $D_4$-symmetric chiral porphyrins, synthesis thereof starting from cyclic ketones and utilization thereof as catalysts, for example, for the asymmetric epoxidation of aromatic alkenes.

2. Description of the Prior Art

The growing demand for enantiomerically pure compounds has stimulated great interest in the development of new asymmetric catalysts. The type most widely employed consist of a catalytically active metal atom bound by a chiral ligand. Metalloporphyrin complexes are a potentially attractive arena in which to explore the rational design of useful asymmetric catalysts. Manganese, iron, and rhodium porphyrins are known to catalyze alkane hydroxylation, alkene epoxidation, cyclopropanation and aziridination, and aluminum porphyrins have been shown to mediate Diels-Alder reactions and initiate the living polymerization of a variety of monomers. Furthermore, the relatively rigid structure of tetraaryl porphyrins provides a general template to which a variety of chiral directing groups can be appended. This should make the rational design of highly enantioselective catalysts somewhat more straightforward than is the case with conformationally mobile ligands. For these reasons, a number of groups have embarked upon such studies. However, despite many innovative approaches, synthetically useful systems have remained elusive. Much of the difficulty can be attributed to the fact that the syntheses of many chiral porphyrins are tedious, inefficient and often inflexible. This a major drawback since the development of highly selective catalysts inevitably involve some empirical experimentation.

Another concern, particularly in the design of asymmetric epoxidation catalysts, is the stability of the porphyrin and the chiral appendages attached to it. Tetraaryl porphyrins bearing electron-donating substituents suffer rapid decomposition of the aromatic macrocycle under the strongly oxidizing conditions employed for these reactions. Furthermore, the active intermediate, a high-valent metal-oxo species, is capable of attacking even unactivated carbon-hydrogen bonds and can therefore consume itself if the chiral appendages are sufficiently flexible to come into contact with the metal center. Since a truly useful asymmetric catalyst must combine high enantioselectivity with high turnover numbers, the problem of oxidative stability is another major factor that must be considered in the design of chiral porphyrins.

We reported a solution to the latter problem several years ago with the synthesis of the "chiral wall" porphyrin 1 (FIG. 1). This chloromanganese (III) derivative of this species proved to be an extremely efficient epoxidation catalyst (over 3000 turnovers using styrenes as the substrate and bleach as the terminal oxidant), presumably since it lacked electron-donating heteroatoms appended to the mesa phenol rings and because the rigid binaphthyl groups could not come into contact with the metal-oxo complex. Unfortunately, the enantiomeric excesses observed ranged from only 10–50%. Even more problematical, the synthesis of aldehyde 2 was relatively tedious and did not lend itself to the straightforward construction of derivatives with different pocket geometries. Finally, the condensation of aldehyde 2 and pyrrole led to three other atropisomers in addition to 1, which necessitated a difficult chromatography purification of the desired α, β, α, β species. A number of other $C_2$-symmetric porphyrins have been constructed in various laboratories, which share the problem of tedious synthetic routes and are less robust than the chiral wall porphyrin.

Halterman and co-workers made an important advance with the synthesis of the first $D_4$-symmetric chiral porphyrin 3 (FIG. 1). These workers also employed a route involving the condensation of a chiral aldehyde and pyrrole to build the porphyfin macrocycle. The symmetry of the product obviated the possibility of obtaining atropisomers, thus greatly simplifying the task of obtaining large quantities of this ligand. The chloromanganese (III) derivative of 3 was found to catalyze the epoxidation of styrenes and cis-1-phenylpropene with respectable enantiomeric excesses. Like the chiral wall porphyrin, ligand 3 also proved to be extremely stable under the reaction conditions and high turnover numbers were obtained. The synthesis of aldehyde 4 was accomplished via a double Diels-Alder reaction between benzoquinone and cyclopentadiene. Transformation of this species to racemic 4 was accomplished in several steps. 4 was resolved by separation of the diastereomeric acetals derived from a chiral diol.

A completely different approach has been employed by Collman and co-workers in the construction of the "threitol-strapped" porphyrins 5 (FIG. 1). In this case, a preformed porphyrin template is coupled to a mixture of isomers of a tetratosylate derived from the condensation of two molecules of 1,4-ditosylthreitol and a bis-aldehyde. This procedure produces three isomers that must be separated. The chloromanganese (III) derivative of the "Out/Out" isomer shown in FIG. 1 catalyzed the epoxidation of aromatic alkenes with e.e.'s ranging from 21% to 88%. However, the strap is oxidatively labile and the threitol-strapped porphyrins are not as robust as the all-hydrocarbon constructions 1 and 3. Nonetheless, this work is significant in that it is the first example of a synthetic approach that can readily produce a family of structurally related porphyrins by simply varying the bis-aldehyde linker and because it employs a cheap, optically active starting material (theritol), thereby avoiding the need to carry out a resolution.

In order to accelerate the development of porphyrin-based asymmetric catalysts, we have invented a synthetic scheme that rapidly and easily produces a new family of structurally diverse and oxidatively robust chiral porphyfin ligands, starting from cheap, optically active materials.

The following prior art references are disclosed in accordance with the terms of 37 CFR 1.56, 1.97, and 1.93.

(1) Groves, J. T.; Nemo, T. E.; Myers, R. S. *J. Am. Chem. Soc.* 1979, 101, 1032.

(2) Ortiz de Montellano, P. R. *Cytochrome P-450: Reactions, Mechanism, and Biochemistry.* Plenum press, 1986.

(3) Callot, H. J.; Metz, F.; Piechoki, C. *Tetrahedron* 1982, 38, 2365.

(4) O'Malley, S.; Kodadek, T. *Organometallics* 1992, 11, 2299.

(5) Groves, J. T.; Takahashi, T. J. *J. Am. Chem. Soc.* 1983, 105, 2073.

(6) Bartley, D. W.; Kodadek, T. J. *Tetrahedron Lett.* 1990, 31, 6303.

(7) Adachi, T.; Sugimoto, H.; Aida, T.; Inoue, S. *Macromolecules* 1993, 26, 1238.

(8) Sugimoto, H.; Aida, T.; Inoue, S. *Macromolecules* 1993, 26, 475 1–4755.

(9) Groves, J. T.; Viski, P. *J. Org. Chem.* 1990, 55, 3628.

(10) Collman, J. P.; Lee, V. J.; Zhang, X.; Ibers, J. A.; Brauman, J. I. *J. Am. Chem. Soc.* 1993, 125, 3834.

(11) Halterman, R. L.; Jan, S.-T. *J. Org. Chem.* 1991, 56, 5253.

(12) Mansuy, D.; Battioni, P.; Renaud, J.-P.; Guerin, P. J. *Chem. Soc., Chem. Commun.* 1985, 155.

(13) Naruta, Y.; Ishira, N.; Tani, F.; Maruyama, K. *Bull. Chem. Soc. Jpn.* 1993, 66, 158.

(14) O'Malley, S.; Kodadek, T. *J. Am. Chem. Soc.* 1989, 111, 9116.

(15) Veyrat, M.; Maury, 0.; Faverjon, F.; Over, D. E.; Ramasseul, R.; Marchon, J.-C.; Turowska-Tyrk, I.; Scheidt, W. R. *Angew. Chem. Int. Ed. Engl* 1994, 33,220.

(16) Sharpless, K. B.; Amberg, W.; Bennani, Y. L.; Crispino, G. A.; Hartung, J.; Jeong, K.-S.; Kwong, H.-L. *J. Org. Chem.* 1992, 57, 2768.

(17) Zhang, W.; Loebach, J. C.; Wilson, S. R.; Jacobsen, E. N. *J. Am. Chem. Soc.* 1990, 112, 2801.

(18) Collman, J. P.; Zhang, X.; Lee, V. J.; Uffelman, E. S.; Brauman, J. I. *Science* 1993, 261, 1404.

(19) Barry, J.; Kodadek, T. *Tet. Lett.* 1994, 35, 2465–2468.

(20) Kiyooka, S. I.; Yamashita, T.; Yamamoto, A.; Fujiyama, R. *Bull. Chem. Soc. Jpn,* 1989, 62, 1364.

(21) Schreiber, J.; Maag, H.; Hashimoto, N.; Eschenmoser, A. *Angew. Chem. Int. Ed. Engl.* 1971, 10, 330.

(22) Rieche; Gross; Hoft *Chem. Ber.* 1960, 93, 88.

(23) Lindsey, J. S.; Schreiman, I. C.; Hsu, H. C.; Kearney, P. C.; Marguerettaz, A. M. *J. Org. Chem.* 1987, 52, 827.

(24) Nuss, J. M.; Rennels, R. A.; Levine, B. H. *J. Am. Chem. Soc.* 1993, 115, 6691.

(25) Leusking, A. J.; Marsman, J. W.; Budding, H. A.; Noltes, J. G.; van der Kerk, G. J. M. *Rec. Tray. Chim.Rec.,* 1965, 567.

(26) Salaun, J.; Fadel, A.; McGee, L. R.; Smart, B. E. *Org. syn.* 1985, 64, 50.

(27) Guilmet, E.; Meunier, B. *Nouv. J. Chem.* 1982, 6, 511.

(28) Collman, J. P.; Kodadek, T. J.; Raybuck, S. A.; Meunier, B. *Proc. Natl. Acad. Sci. USA* 1983, 80, 7039.

(29) Lindsey, J. L.; Wagner, R. W. *J. Org. Chem.* 1989, 54, 828.

(30) Dolphin, D.; Camenzind, M. J.; James, B. R.; Sparapany, J. W.; Ibers, J. A. *Inorg. Chem.* 1988, 27, 3054.

(31) Collman, J. P.; Brauman, J. I.; Meunier, B.; Hayashi, T.; Kodadek, T. J.; Raybuck, S. A. *J. Am. Chem. Soc.* 1985, 107, 2000.

(32) Comins, D. L.; Dehaghani, A. L. *Tetrahedron Lett.* 1992, 33, 6299.

(33) Lipshutz, B. H.; Keil, R.; Barton, J. C. *Tetrahedron Lett.* 1992, 33, 5861.

(34) Coxon, J. M.; Dansted, E.; Hartshorn, M. P.; Richards, K. E. *Tetrahedron.* 1968, 24, 1193.

(35) van Rheenen, V.; Kelly, R. C.; Cha, D. Y. *Tetrahedron Lett.* 1976, 23, 1973.

(36) Seitz, D. E.; Lee, S.-H. *Tetrahedron Lett.* 1991, 22, 4909.

(37) Brown, C. A.; Jadhav, P. K. *Org. Syn.* 1987, 65, 224.

All of the above-cited prior an and any other references mentioned herein are incorporated hereby by reference in their entirety. These references relate to porphyrin chemistry and are the leading edge in this technology.

SUMMARY OF THE INVENTION

The present invention provides a novel synthesis of $D_4$-symmetric chiral porphyrins (FIG. 1, formula 7) derived from 1R(+)-nopinone. The simplicity and flexibility of this synthetic protocol provides an attractive route to this novel class of porphyrins starting from cyclic ketones. For example, the chloromanganese (III) derivatives of the new macrocycles have utility as catalysts for the asymmetric epoxidation of aromatic alkenes, among other compounds.

DETAILED DESCRIPTION OF THE INVENTION

The present invention will be discussed with regard to FIGS. 1–6 and the aforementioned prior art references, i.e. numbers 1–37.

The present invention, in part, provides a novel synthetic route to new chiral $D_4$-symmetric porphyrins with a general structure in which identical carbocylic tings containing one or more asymmetric centers are fused above and below each of the mesoaromatic rings. This new class of compounds was found to be important because of the presence of the carbocyclic rings render the chirality much more rigid than would be the case in an acylic system. It was found that these compounds could be made from a condensation reaction between pyrrole and the appropriate chiral aldehyde and thus, the process provides short, efficient and inexpensive starting materials.

Figure 1:
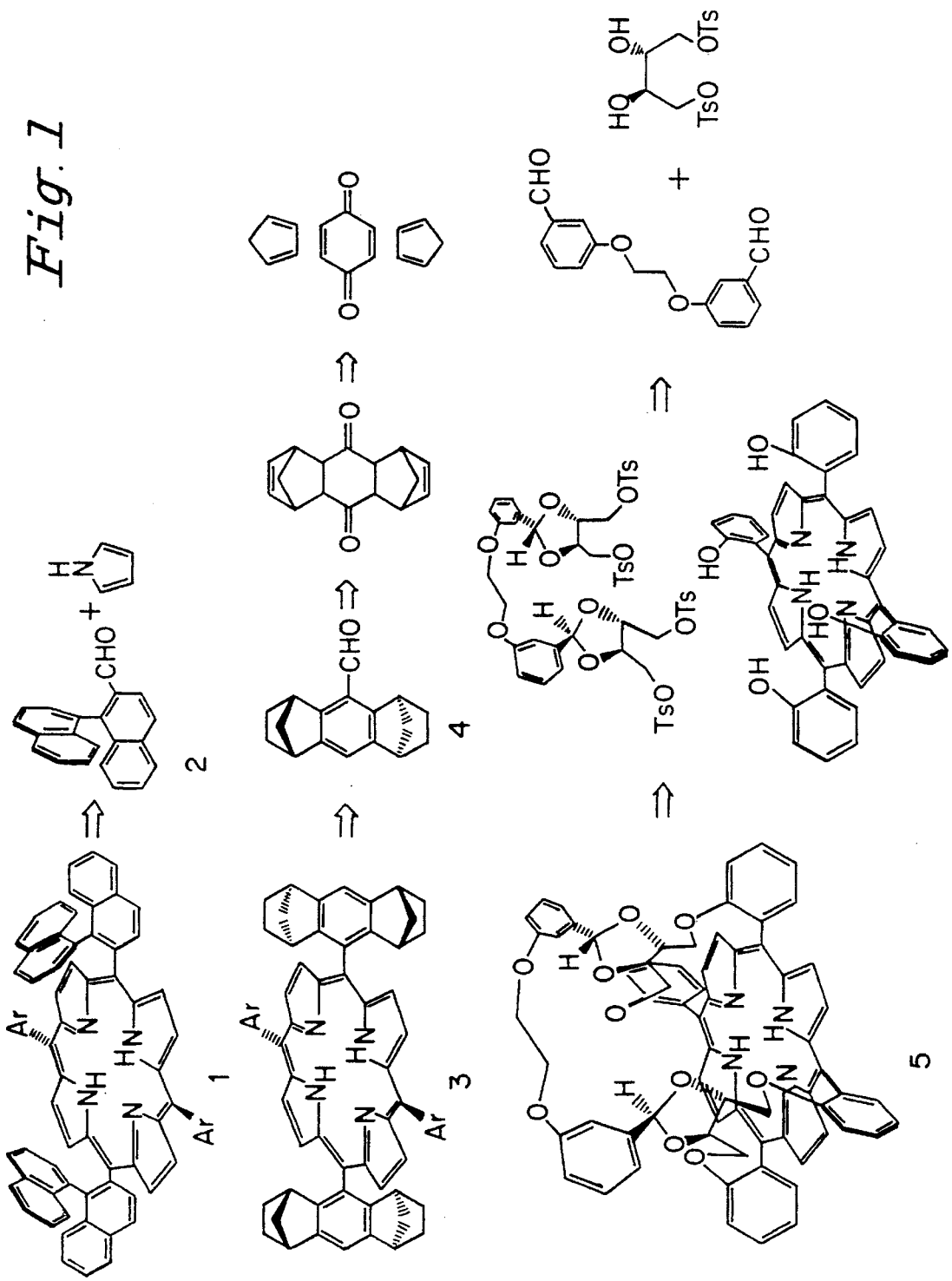
Figure 2:
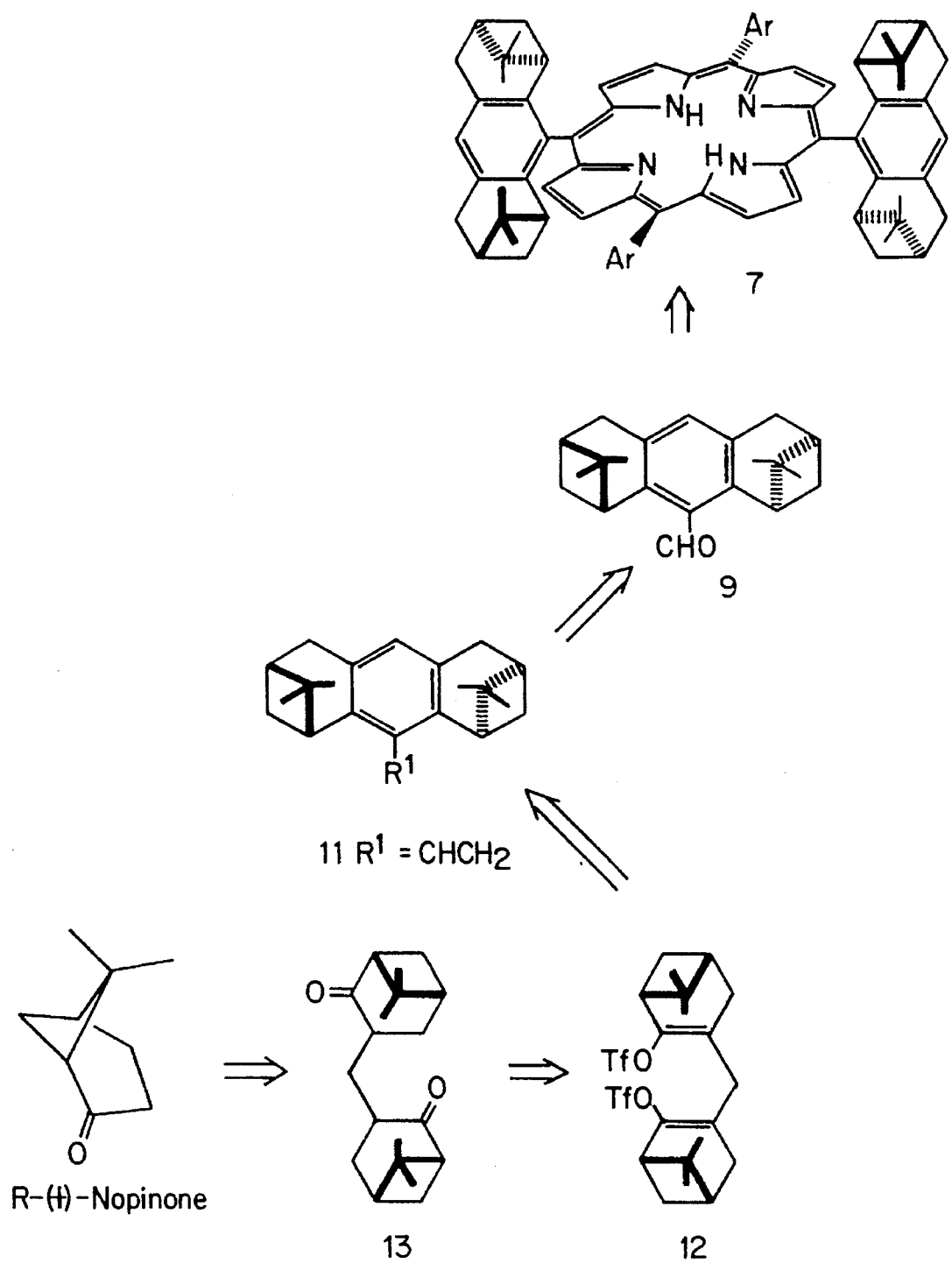

The novel porphyrins produced by these new processes are exemplified by the porphyfin shown in FIG. 2 (formula 7). Retrosynthetically, macrocycles were derived from aldehydes. This aldehyde contains a central aromatic ting flanked by cycles derived from the commercially available terpene R-(+)-nopinone. The first step was linking the nopinone-derived rings by a methylene bridge and then closing the aromatic ting using a type of "5+1" condensation to provide the central aromatic ring.

The first step in the overall process involves the addition of nopinone in DMF to a suspension of potassium hydride in THF at 40°–50° C. This gives 1,5-diketone 13 in 60% yield when conducted on a 15 gram scale or less. However, this reaction was somewhat capricious when carried out on a larger scale, and often gave lower yields of the diketone (typically 10–20%), providing the or-methylene derivative of nopinone as the major product. An alternative preparation of 13 was found which involves the addition of Eschenmoser's salt to a two-fold molar excess of the potassium enolate of nopinone in THF (58%). This procedure was found to be reproducible even on a large scale.

The second step in the overall process is to transform the 1,5-diketone into an aromatic ring. This new method involves the double deprotonation of 13 with KHMDS, cooling of the bis-enolate to –78° C., and the addition of Commin reagent[Comin, 1992 #25] (5-chloro-2-bistriflylamino-pyridine) to yield bis-enoltriflate 12 in 65% yield after column chromatography (FIG. 2).

Figure 3:
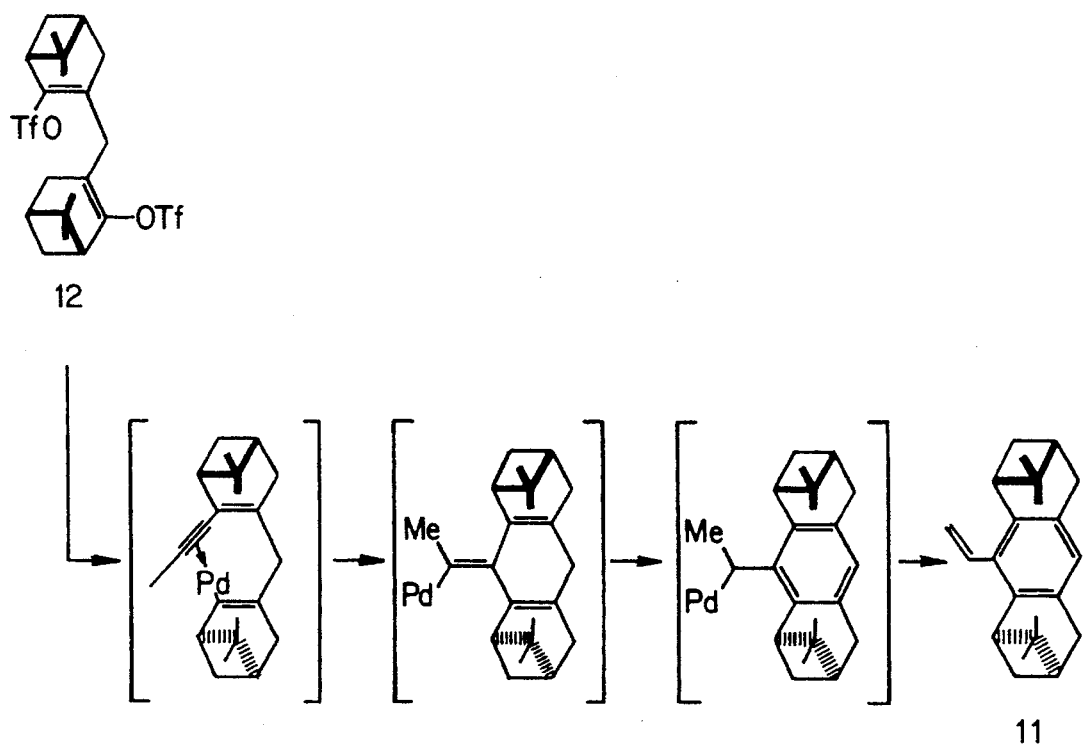

The third step of the present invention relates to the preparation of 11 from 12. This was accomplished by treatment of 12 with 1-tributylstannyl-propyne in the presence of palladium tetrakis(triphenylphosphine) in DMF from which a 25% yield of styrene 11 was obtained. The conversion of 12 to 11 proceeds through subsequent reactions (FIG. 3). In this step, a vinylpalladium intermediate is produced, which isomerizes to a benzylic alkylpalladium complex which then undergoes β-hydride elimination to provide the vinyl group in 11.

Figure 5:
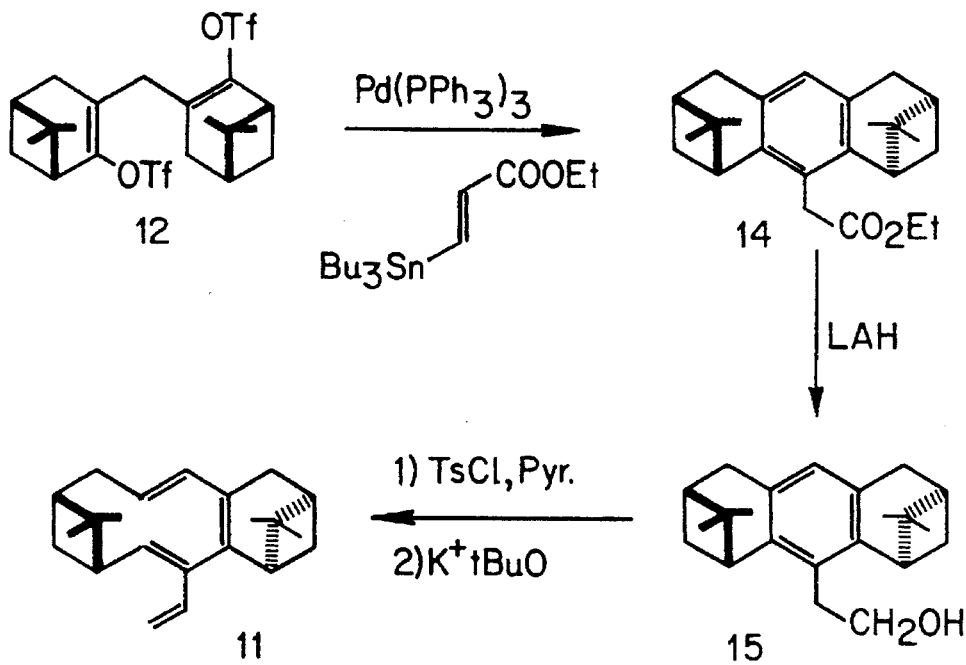

This third step of the transformation of 12 to 11 can also be accomplished according to the alternative route shown in FIG. 5. Tributyltin-2-ethyl acrylate was substituted for the pentynylstannane in a common Stille/Heck sequence, providing ester 14, which was then reduced using LiAlH$_4$ (THF,-78° C.) to give alcohol 15 in 96% yield. 15 was then treated with p-toluene sulfonyl chloride (4.2-fold molar excess) and the resulting mixture was added directly to potassium tert-butoxide in DMSO to provide styrene 11 in 64% yield. The overall yield of these three operations (in step 3) was about the same as the one-step protocol employing the alkynyl stannane. For small scale applications, the more direct route using the propynyl stannane is preferred, but because of the large amount of palladium catalyst required for this reaction, the route shown in FIG. 5 is more practical for large scale preparations.

Figure 4:
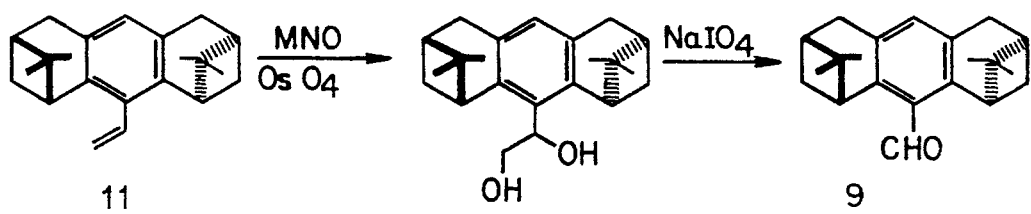

In the fourth step, the vinyl group was then cleaved oxidatively in two sequences (catalytic $OsO_4$, N-morpholine oxide, followed by $NaIO_4$, 60% overall to give the desired aldehyde 9 (FIG. 4).

In the fifth step, condensation of 9 with pyrrole under Lindsey conditions yields porphyrin 7.

Thus, the new porphyrins of the present invention are prepared by the novel process outlined above and can be summarized as follows: A process for preparing a porphyrin which comprises the steps of (1) reacting an optically active ketone under suitable coupling conditions to produce a diketone; (2) enolizing said diketone under suitable conditions, followed by converting said enolized diketone under suitable conditions to form a bis-enoltriflate; (3) reacting said bis-enoltriflate with a suitably substituted vinyl or alkynl stannane in the presence of a catalyst to form a substituted arenyl alkene; (4) oxidizing said alkene to form the corresponding aldehyde; and (5) condensing said aldehyde with pyrrole to form said porphyrin.

This new porphyrin 7 (FIG. 2) is the basic ligand/structure for the new (metal-containing) catalysts of the present invention.

In order to prepare the metal-ligand complex, porphyrin-based catalyst, the following step is required.

Figure 6:
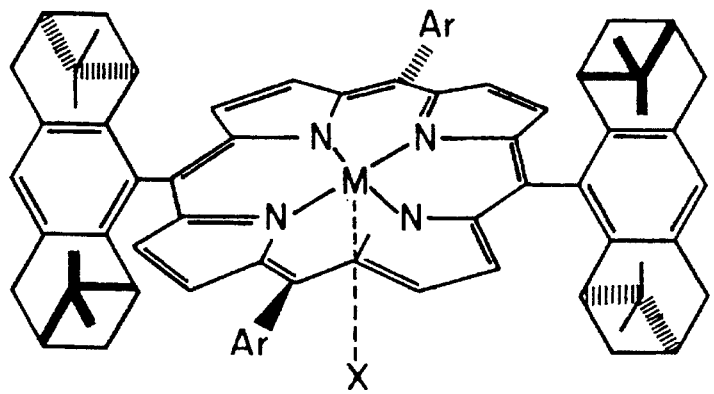

In this step, the metalation of the new porphyrin 7, is accomplished by the addition of a metal salt "MX"), e.g. $MnBr_2$ to such porphyrin, refluxing for a sufficient period of time, e.g. one minute to 12 hours, washing the resulting material with a mineral acid to finally form the metal-containing catalyst shown in FIG. 6. The "MX" designation is where M stands for a metal selected from the group consisting of manganese (Mn); iron (Fe); aluminum (Al); rhodium (Rh); nickel (Ni); cobalt (Co); ruthenium (Ru); and copper (Cu). X stands for any counterion such as chlorine (Cl); bromine (Br); iodine (I); boron tetrafluoride ($BF_4$); and phosphorus hexafluoride ($PF_6$).

In another facet of the present invention, there is also provided new metal-containing porphyrin-based catalysts having substituted imidazoles as axial ligands; this axial ligand is represented by the formula:

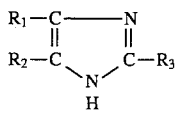

where $R_1$, $R_2$, and $R_3$ are equal or non-equal and are independendently selected from the group consisting of H, alkyl $C_1$-$C_8$, cyclic alkyl, and aromatics (phenyl, naphthyl). Examples of such axial ligands include (1) DCI- 1,5-dicyclohexyl imidazole and (2) IAP - 4'-imidazol-1-yl)acetophenone. It is not understood how these axial ligands are exactly attached to the metal-ligand complex (FIG. 6) and Applicants do not wish to be limited to any theory thereof. The experimental results, disclosed herein, however prove that such axial ligands are effective.

In another facet of the present invention, it has been found that these new metal-porphyrin complexes can be used as efficient catalysts for a number of reactions, including (without limitation) alkene cyclopropanation, epoxidation, alkane hydroxylation, and the like. In this pan of the present invention then, there is encompassed the carrying out of any known conventional syntheses in an asymmetric fashion in which the catalyst thereof is replaced by the novel metal-containing porphyrins (with or without axial ligands) as disclosed above.

This facet of the present invention thus relates to asymmetric syntheses in which a prochiral or chiral compound is reacted in the presence of optical, metal-ligand complex catalyst to produce an optically active product.

Specifically, it has been unexpectedly found that the new porphyfin catalyst, disclosed in the earlier part of this specification, can effect asymmetric synthesis in various processes with various substrates to produce a specific isomeric material with high enantiomeric excess (ee) and which is optically active.

The processes of this pan of the invention are distinctive in that they provide good yields of optically active products having high stereoselectivity, high regioselectivity, and good reaction rate without the need for optical resolution. The processes of this part of the invention stereoselectively produce a chiral center. An advantage of this invention is that optically active products can be synthesized from inexpensive optically inactive reactants. Another advantage is that yield losses associated with the production of an undesired enantiomer can be substantially reduced.

The asymmetric syntheses processes of this invention are useful for the production of numerous optically active organic compounds, e.g. epoxides, aldehydes, alcohols, ethers, esters, amines, amides, carboxylic acids, and the like, which have a wide variety of applications.

The asymmetric syntheses processes can be conducted in continuous, semicontinuous, or batch fashion and involve a liquid recycle and/or gas recycle operation as desired. Likewise, the manner or order of addition of the reaction ingredients, catalyst, and solvent are also not critical and may be accomplished in any conventional fashion.

In general, the asymmetric syntheses reactions are carried out in a liquid reaction medium that contains a solvent for the catalyst, preferably one in which the reaction ingredients, including catalyst, are substantially soluble.

As indicated above, the subject invention encompasses the carrying out of any known conventional syntheses in an asymmetric fashion in which the prior an catalyst thereof is replaced by an optical metal-ligand complex catalyst as disclosed herein.

The process of this pan of the present invention, for example, contemplates using these highly active porphyrin catalysts for convening alkenes to epoxides at high selectivity, by reacting the alkenes with the catalyst in a homogenous reaction phase. The catalyst is introduced into the reaction vessel dissolved in a liquid medium, or slurried, or otherwise dispersed in a liquid medium to eventually provide a homogeneous reaction phase. Suitable solvents are, e.g. alcohols, ethers, ketones, paraffins, cycloparaffins, and aromatic hydrocarbons and chlorinated hydrocarbons.

Feeds constituted of, or feeds containing alkenes such as alpha olefins, particularly straight chain alpha olefins, having from two to about 20 carbon atoms ($C_2$ to $C_{20}$), preferably from about $C_2$ to $C_{12}$, are preferred. The alpha olefins are characterized by a terminal double bond, i.e., $CH_2$=CH—R, and these groups may be substituted if the substituents do not interfere in the epoxidation reaction. Exemplary of such substituents are carbonyloxy, oxy, alkoxy, phenyl, and the like. Exemplary alpha olefins, or olefins unsaturated in the 1-position, include alkenes, alkyl alkenoates, alkenyl alkyl ethers, alkenols, and the like, e.g., ethylene, propene, 1-butene, 1-pentene, 1-hexene, 1-heptene, 1-octene, vinyl acetate, allyl alcohol, and the like.

The feed is contacted with the catalyst at temperature, pressure, and time sufficient to convert the alkenes to epoxides at high selectivities. In general, the temperature of the reaction ranges from about −10° C. to about 150° C., preferably from about 0° C. to about 10° C. In general, total pressures range from about 15 pounds per square inch (psi) to about 300 psi.

The catalyst is generally employed in the reaction mixture in concentrations ranging from about $10^{-5}$M to about $10^{-2}$M (molarity). After the catalyst is added to the reaction vessel as a slurry or a solution, the reaction is brought to the desired operating temperature. The feed is then introduced into the reaction vessel to commence an operation. Alkene feeds that are liquids at or near room temperature (e.g., 1-hexene, 1-octene) are introduced to the reaction zone prior to charging the other reactants, although this is not a prerequisite for the reaction. The process is suited to batchwise operation, or to continuous operation via the use of suitable apparatus.

The following examples are further exemplary of the active and highly selective porphyrin-based catalysts of this invention for the use in conducting epoxidation reactions. In the examples and demonstrations that follow, all parts are in terms of mole units, pressures in terms of pounds per square inch gauge, and temperatures expressed in terms of degrees Centigrade, except as otherwise expressed.

In conducting this series of tests, it was found that the porphyrin-based catalysts of this invention produce epoxidation of the alkene feed under very mild conditions.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

In conjunction with the following examples, the general procedures used are outlined as follows: All $^1$H NMR spectra were recorded at 300 MHz as solutions in deuterochloroform (CDCl$_3$). Chemical shifts are reported in pans per million (ppm, δ) downfield from tetramethylsilane (TMS) (δ=0.00 ppm) and are referenced to the deuterated solvent. Splitting patterns are designated as s, singlet; d, doublet; dd, double-doublet; dt, double-triplet; dq, double-quartet; t, triplet; q, quartet; p, pentuplet; m, multiplet; comp, complex multiplet; br, broad. Coupling constants are given in hertz (Hz). $^{13}$C NMR spectra were recorded at 75.5 MHz as solutions in CDCl$_3$. Chemical shifts are reported in pans per million (ppm δ) downfield from tetramethylsilane (TMS) (δ=0.00 ppm) and are referenced to the deuterated solvent. IR spectra were recorded on a Perkin-Elmer 1600 FT instrument, either from thin films of chloroform solutions or on sodium chloride plates, and reported in wavenumbers (cm$^{-1}$). Mass spectra were obtained using chemical ionization unless stated otherwise. Gas chromatographic analyses were performed using a Hewlett-Packard HP-5890 instrument equipped with a flame ionization detector and a HP-3393A integrator. Experiments utilizing moisture-sensitive reagents were done under a positive argon atmosphere. THF was distilled over sodium/benzophenone. Dichloromethane (CH$_2$Cl$_2$) was distilled from a calcium hydride suspension. All other materials and anhydrous solvents were used as obtained from commercial sources, unless otherwise stated. Preparative column (flash) chromatography was carded out using 60H silica gel (Merck 9385). Compositions of solvent mixtures are quoted as ratios of volume. Commins' reagent (5-chloro-2-bistrifylamino-pyridine) was prepared according to the literature procedure.[32] Tributyltin-1-propyne was prepared according to the method of Lipshutz.[33] 1R-(+)-Nopinone is commercially available or can be prepared conveniently on a large scale from pinane-2α-10-diol[34] by oxidative cleavage with sodium metaperiodate. Pinane-2α, 10-diol was prepared by osmylation of β-pinene, according to the method of van Rheenan; (van Rheenan, V.; Kelly, R. C.; Cha, D. Y.—*Tetrahedron Lett.* 976, 23, 1973, and which article is incorporated herein by reference in its entirety).

EXAMPLE 1

Preparation of Methylene bis [3,3'-(6,6-dimethylbicyclo[3.1.1]heptan-2-one] 13.

(a) Potassium hydride (35% wt. mineral oil dispersion, 12.6 g, 0.11 mol) was washed with anhydrous hexane (3×50 mL). The flask was then charged with anhydrous DMF (100 mL). A solution of 1R-(+)-nopinone (12.84 mL, 13.8 g, 0.1 mol) in dry THF (60 mL) was prepared and added slowly to the hydride suspension. The mixture was then stirred for three hours at 50° C. after which time the reaction mixture was cautiously quenched with 5% HCl (300 mL) at 0° C. The product was then extracted into ethyl acetate (300 mL) and washed with a saturated NaCl solution (300 mL). The organic layer was then separated and dried over MgSO$_4$, followed by solvent removal to give a white, waxy solid. This material was dissolved in hot ethyl acetate (40 mL) and diluted with hexane (200 mL). Cooling of this solution yields 13 as white crystals (8.64 g, 60% yield);

mp 155° C.; $v_{max}$1702 cm$^-$; $^1$H NMR. δ 2.6 (dt, J=11, 3, 2H), 2.49 (t, J=5, 2H), 2.32 (p, J=5, 2H), 2.2 (m, 2H), 2.15 (m, 2H), 1.85 (t, J=8, 2H), 1.59 (d, J=11, 2H), 1.39 (dd, J=13, 9, 2H), 1.19 (6H, s), and 0.6 (6H, s); $^{13}$C NMR δ 2.16., 58., 43., 41., 39., 29.9, 28.5, 26.5, 25.5, and 21; m/z 289 [M$^+$+1(100%)], 271 (15), 154 (10), and 139 (15).

HRMS calculated for C$_{19}$H$_{28}$O$_2$ M$^+$ 288.2089, found 288.2095. Larger scale repetition (20 g or more) of this procedure resulted in an endothermic reaction if nopinone was added too quickly, and frequently yielded 3-Exomethylene-1-R-(+)-nopinone (58% yield);

bp 90°–100° C./0.2 torr); $v_{max}$1708 cm$^{-1}$; $^1$H NMR. δ 6.4 (d, J=3, 1H), 5.45 (d, J=3, 1H), 2.83 (m, 2H), 2.69 (dt, J=6.4, 1.28, 2H), 2.33 (m, 1H), 1.53 (dr, J=10.7, 2, 1H), 1.43 (s, 3H) and 0.9 (s, 3H); $^{13}$C NMR δ 202., 140., 122., 55.5, 40.5, 39, 30, 26.5, 25.9, and 21.5; m/z 151 [M$^+$+1(100%)], 150 [M$^+$(9%)], 133 (13), 123 (17), and 109 (10). HRMS calculated for C$_{10}$H$_{14}$O (M$^+$+1) 151.1123, found 151.1126; [α]$_D$= +26 (c=2, CH$_2$Cl$_2$.

(b) Potassium hydride (35% wt. mineral oil dispersion, 64 g, 0.56 mol) was washed with anhydrous hexane (2×100 mL). Anhydrous THF (150 mL) was added and the resultant suspension was cooled in an ice bath. 1R-(+)-Nopinone (69 mL, 74.6 g, 0.54 mol) was then introduced slowly. This mixture was then allowed to stir for 180 minutes and gave a cream-colored suspension. N,N-Dimethylmethyleneammonium iodide (Eschenmoser's salt, Schreiberm, J.; Maag, H.; Hashimoto, N.; Eschenmoser, A. *Angew. Chem. Int. Ed. Engl.* 1971, 10, 330; and which reference is incorporated herein by reference in its entirety) (50 g, 0.27 mol) was then added in small portions (2 g) over 60 minutes. This suspension was then allowed to stir for 60 minutes and the solution was left to reflux gently for a further 12 hours. The reaction was followed by TLC (hexane:ethyl acetate 4:1) and the least polar 3-exomethylene-1-R-(+)-nopinone (rf 0.8) was observed during the course of the reaction. Extra Eschenmoser's salt (20 g, 0.11 mol) was added after 24 hours and the remaining nopinone was consumed within 4 hours. The reaction mixture was then worked up as previously described, giving crystals of 13 (42 g, 54% yield), mp 155° C.

EXAMPLE 2

Preparation of methylene bis[3,3'-(6,6-dimethylbicyclo [3.1.1] heptenyl-2-triflate] 12.

To a solution of 13 (6 g, 21 mmol) in THF (60 mL), KHMDS [0.5 molar solution in toluene (88 mL, 42 mmol)] was added slowly at room temperature (RT) to give a light brown colored solution. After 30 minutes the solution was cooled to −78° C. A solution of freshly prepared 5-chloro-2-bistrifylamino-pyridine (16.49 g, 42 mmol) in THF (40 mL) was then added over 10 minutes. The reaction mixture was allowed to warm to RT, and stirred for a further 10 hours. Brine (200 mL) was then added to the mixture and the product was extracted into ethyl acetate (200 mL), washed with cold NaOH (10% aqueous). The organic layer was dried (anhydrous $K_2CO_3$), filtered, and the solvent was removed in vacuo to give a yellow oil. 12 was then purified by chromatography (silica/hexane: ethyl acetate 4:1) to give a colorless oil (7.56 g, 65% yield);

$v_{max}$, 2939, 1421, 1209, 1055, and 999 cm$^{-1}$; $^{-1}$H NMR 3.15, (s, 2H), 2.6 (dr, J=8, 5, 2H), 2.49 (t, J=5, 2H), 2.29 (br t, 4H), 2.19 (comp, 2H), 1.39 (s, 6H), 1.35 (d, 2H), and 0.9 (s, 6H); $^{13}$C NMR 151.5, 121.5, 119.5, (q, J=340, $CF_3$), 47, 42, 41.5, 31.9, 31.5, 28, 26.3, and 21; m/z 553 (M$^+$+1, 7.3%), 552 (M$^+$, 6.5), 422 (61), 404 (49), 404 (100), 359 (58), 283 (70), 270 (71), 270 (80), and 253 (100). HRMS calculated for $C_{21}H_{26}O_6F_2S_2$ (M$^+$) 552.1075, found 552.1077.

EXAMPLE 3

Preparation of 9-vinyl-2,2,7,7,-tetramethyltricyclo[3.1.1]-1,3-6,8-methylene-4,5-dihydroanthracene 11 from 12 with tributyltin-1-propyne.

The bistriflate 12 (0.15 g, 0.27 mmol), LiCl (0.060 g, 1.4 mmol.), tetrakis(triphenylphosphine)-palladium(0) (0.16g, 0.14 mmol, 0.5 equiv), and triethylamine (0.1 mL, 0.072 g, 0.7 mmol) was dissolved in DMF (5 mL) at 75° C. Tributyltin-1-propyne (0.43 g, 1.3 mmol, 4.5 equiv) in DMF (5 mL), was then added dropwise to 12 over 2 hours at 75° C. The reaction mixture was poured into saturated NaCl solution (20 ml) and then added to ethyl acetate (50 ml). The organic layer was then separated, stirred with activated charcoal, dried over $MgSO_4$, and filtered. Removal of the solvent under reduced pressure gave the product as a yellow oil. The product was further purified by column chromatography (silica/hexane) to give a white solid (0.02 g, 24% yield). This material was dissolved in pentane and gave crystals of 11 that were white square platelets;

mp 107° C.; $v_{max}$, 2908, 1682, and 1681 cm$^{-1}$; $^1$H NMR δ 6.75 (s, 1H), 6.5 (dd, J=17.3, 11.3, 1H), 5.25 (dd, J=11.3, 2.3, 1H), 4.75 (dd, J=17.3, 2.3, 1H), 2.9 (t, J=7, 2H), 2.8 (m, 4H), 2.4 (dt, J=8, 5, 2H), 2.1 (comp, 2H), 1.21 (s, 6H), 1.05 (d, J=9, 2H), and 0.55 (s, 6H); $^{13}$C NMR δ 141, 134.5, 133, 131.5, 126, 119.5, 43, 40, 28.5, 33, 31.7, 26.5, and 21.5; m/z 293 (M$^+$+ 1 (100%), 292 (M$^+$65%), 291 (32), 277 (22), 249 (33), and 211 (13.5). HRMS calculated for $C_{22}H_{28}$(M$^+$) 292.2199, found 292.2191; [α]25$_D$=−0.459 (C=2.0, $CH_2Cl_2$).

EXAMPLE 4

Preparation of cis and trans-B-tributyltin ethylacrylate.

These organotin reagents were prepared in a similar manner as that described by Marsman et al (Leusking, A. J.; Marsman, J. W.; Budding, H. A.; Noltes, J. G.; van der Kerk, G. J. M. Rec. Trav. Chim. Rec., 1965, 567, and which publication is incorporated herein by reference in its entirety). Thus, a mixture of ethyl propiolate (10 mL, 9.68 g, 0.099 mol), tributyltin hydride (31.3 mL, 33.94 g, 0.116 mol) and AIBN (0.05 g, 0.3 mmol) was heated at 50° C. for 12 hours. Vacuum distillation of the reaction mixture gave β-tributyltin ethylacrylate (28.4 g, 74%, bp 120°–160° C./0.2 torr) as a mixture of the cic and trans isomers. The $^1$H NMR spectrum showed two pairs of doublets, one set at δ 6.25 (J=19.65) and 7.7 ppm (J=19.65) that corresponded to the trans isomer. The other set (cis isomer), was at δ 7.15 (J=13) and 6.75 (J=13). These values are in agreement with those published by Seitz[36]. The ratio of cis to trans isomers was 1.44:1 according to the integral value.

EXAMPLE 5

Preparation of Ethyl-(2,2,7,7,-tetramethyltricyclo[3.1.1]-1,3-6,8-methylene-4,5 -dihydroanthracenyl-9)-acetate 14.

Tetrakis(triphenylarsine)-palladium(0) was prepared in-situ under an argon atmosphere by dissolving tris(dibenzylideneacetone)-dipalladium(0) (1.141 g, 1.25 mmol, 3 mol. %), triphenylarsine (3.1g, 10.05 mmol) in NMP (150 mL) to give a yellow-colored solution. Each of the following materials was then added; LiCl (10.57 g, 0.245 mol. 3.1 equiv), bistriflate 12 (44.6 g, 80.5 mmol), and dry triethylamine (35 mL, 25.2 g, 0.245 mol). The reaction mixture was then placed in an oil bath at ca 70° C. and stirred mechanically. To this mixture a solution of cis and trans-2-n-butyltin ethyl acylate (35.62 g, 91.7 mmol) in NMP (75 mL) was added over 6 hours. Stirring was then continued for a further 5 hours at 70° C. The reaction mixture was then poured into brine (500 mL) and the product was extracted into ethyl acetate (250 mL). The organic layer was then separated, stirred with activated charcoal, dried over $MgSO_4$ and then filtered through a silica plug. Removal of the solvent under reduced pressure gave the product as a yellow oil. The product was further purified by column chromatography [silica/hexane/ethyl acetate (9:1)] to give a yellow waxy solid (24.2 g), $^1$H NMR analysis showed this material to contain organic impurities (~22%) that were difficult to separate from the desired product (calculated yield 18.9 g, 66.7%).

mp 95° C.; $^1$H NMR δ 6.8 (s, 1H), 4.05 (q, J=7, 2H), 3.5 (s, 2H), 3.05 (t, J=4, 2H), 2.9 (m, 4H), 2.5 (dr, J=8, 4, 2H), 2.2 (comp, 2H), 1.39 (s, 6H), 1.3 (d, J=9, 2H), 1.1 (t, J=7, 3H), and 0.6 (6H, s); $^{13}$C NMR 15 172, 142, 131.9, 127, 126, 60, 43.5, 40.5, 33.5, 31.9, 26.5, 21.5, 17.5, 14.3, and 13.5; m/z 353 (M$^+$+1) (100%), 352 (M$^+$+ 60%), 339 (28), 309 (25), 307 (16), 281 (15), 280 (19), 279 (77), 273 (100), 235 (25), and 223 (19). HRMS calculated for $C_{24}H_{32}O_2$ (M$^+$+1) 353.2481, found 353.2465.

EXAMPLE 6

Preparation of the alcohol 15 by reduction of 14.

The ester 14 (18.9g, 54 mmol) in THF (100 ml) was added cautiously to a 1 molar THF solution of Lithium aluminum hydride (340 mL, 0.34 mol) at $-78°$ C. and then allowed to stir for 4 hours while warming to RT. The reaction mixture was then cooled in an ice/water bath and saturated aqueous $Na_2SO_4$ (500 cm$^3$) was added slowly over 30 minutes. The resultant white precipitate was removed by filtration and washed with ethyl acetate (250 mL). The filtrate was then combined and the organic layer separated, dried ($MgSO_4$), and filtered. Removal of the solvent under reduced pressure gave the product as a colorless oil. Column chromatography [silica/hexane/ethyl acetate (9:1)] gave a white semicrystalline material (16 g, 96%);

mp 103° C.; $v_{max}$3523, 2980, and 2917 cm$^{-1}$; $^1$H NMR δ 6.75 (s, 1H), 3.4 (br s, 2H), 3.1 (t, J=6, 2H), 2.9 (m, 4H), 2.8 (t, J=6, 2H), 2.6 (dt, J=11, 5, 2H), 2.2 (comp, 2H), 1.6 (s, 1H), 1.39 (s, 6H), 1.2 (d, J=9, 2H), and 0.6 (s, 6H); $^{13}$C NMR δ 142, 134, 132, 126.5, 64, 43, 40.5, 39, 33, 31, 30.5, 26.5, and 21.5; m/z 311 (M$^+$+1 (39%), 310 (M$^+$55%), 309 (45), 295 (25), 294 (49), 293 (100), and 267 (13). HRMS calculated for $C_{22}H_{30}O$ (M$^+$) 310.2296, found 310.2281.

EXAMPLE 7

Preparation of 9-vinyl-2,2,7,7,-tetramethyltricyclo[3.1.1]-1,3-6,8-methylene-4,5 -dihydroanthracene 11 from alcohol 15.

Anhydrous pyridine (100 mL), the alcohol 15 (16.0 g, 51.6 mmol), and 4-dimethylaminopyridine (0.05 g, 0.4 mmol) was stirred in THF (100 mL). This solution was cooled in an ice bath and p-toluene sulfonyl chloride (43 g, 0.227 mol, 4.4 equivalent) was added cautiously. The resultant solution was then allowed to warm to room temperature. After 12 hours, the reaction mixture was added to a solution of $^t$BuOK (100 g, 0.89 mol) in anhydrous DMSO (300 mL) at 40° C. over 30 minutes. The mixture was then delivered to an ice/water bath (200 mL), and acidified with 10% aqueous HCl (300 mL). The product 11 was then extracted into ethyl acetate (300 mL), dried over $MgSO_4$ and filtered. Evaporation of the solvent gave a dark brown tar. Chromatography [silica/pentane/ethyl acetate (100:1)] gave a yellow waxy material (10 g, 66%). This material was dissolved in hot pentane and gave crystals of 11 (8.84 g, 58.6%);

mp 107° C.; $[α]_D = -0.459$ (C 2.0, $CH_2Cl_2$).

EXAMPLE 8

Preparation of 2,2,7,7,-tetramethyltricyclo[3.1.1]-1,3-6,8-methylene-4,5 -dihydroanthracen-9-carboxaldehyde 9.

The alkene 11 (2.5 g, 8.6 mmol) was dissolved in acetone (50 mL). To this solution, N-methyl morpholine-N-Oxide [60% wt. aqueous solution (15 mL, 9 g, 76 mmol)] was added. This mixture was then allowed to stir with Osmium tetroxide (1.5 mL of 2.5 wt. % $^t$BuOH solution, 0.98 mmol). After 22 hours, sodium metabisulfite (60 g, 0.32 mol) was added cautiously and stirring was continued for another 5 hours. This suspension was then filtered and the resultant diol extracted from the filtrate with ethyl acetate (150 mL), dried over $Na_2SO_4$ and refiltered. Removal of the solvent gave an oily residue. The diol was then isolated by column chromatography [silica/hexane/ethyl acetate (4:1)] to give a white powder (2.2 g). This powder was dissolved in hexane and gave white opaque crystals (1.77 g, 63.3%);

mp 94° C.; $v_{max}$3393, 2910, and 1731 cm$^{-1}$; $^1$H NMR δ 6.8 (s, 1H), 5.5 (dt, 1H), 4.0 (2H, m), 3.8 (m, 2H), 3.2 (m, 4H), 3.1 (br s, 2H), 2.95 (m, 2H), 2.5 (m, 2H), 1.79 (s, 6H), 1.5 (d, 2H), and 0.95 (s, 6H); $^{13}$C NMR δ 141.5, 141, 132.5, 132, 131.2, 130.9, 127.9, 71.5, 71, 66.1, 66, 43.5, 43, 40, 38.5, 38 34.9, 31.75, 31.7, 26.2, and 21.5; m/z 327 (M$^+$+1 (2%), 326 (M$^+$5), 309 (65), 295 (87), 291 (100), 265 (88), and 265 (88). HRMS calculated for $C_{22}H_{30}$ (M$^+$) 326.2246, found 326.2243.

The diol (1.12 g, 3.4 mmol) was dissolved in absolute ethanol (25 mL), and distilled water (16 mL) was added dropwise to give a homogeneous mixture. A solution of sodium periodate (0.77 g, 3.6 mmol) in water (6 mL) was then added slowly. After 30 minutes, 9 was extracted into ethyl acetate (20 mL), the organic layer was then separated, dried over $MgSO_4$ and filtered. Removal of the solvent under reduced pressure gave a white powder (0.98 g). The product was then isolated by column chromatography [silica/hexane], and recrystallized from pentane giving transparent needles (0.88 g, 87%);

mp 113° C.; $v_{max}$1681 cm$^{-1}$; $^1$H NMR δ 10.4 (s, 1H), 7.0 (s, 1H), 3.55 (t, J=5, 2H), 2.9 (m, 4H), 2.6 (dt, J=9, 5, 2H), 2.25 (comp, 2H), 1.4 (s, 6H), 1.2 (d, J=5, 2H), and 0.65 (6H, s); $^{13}$C NMR δ 194.5, 145.5, 133, 132.7, 130.5, 42, 39.9, 38.5, 33.5, 31.5, 26.3, and 21.5; m/z 295 (M$^+$+1 (100%), 294 (M$^+$20), 293 (16), 279 (9), and 267 (11); HRMS calculated for $C_{21}H_{26}$ O (M$^+$+1 ) 295.2061, found 295.2056; $[α]^{25}_D = -11.4$, (C=2.0, $CH_2Cl_2$).

EXAMPLE 9

Determination of enantiomeric purity of aldehyde 9.

The enantiopurity of 9 was determined by the addition of small aliquots of tris[3 -(heptafluoropropylhydroxy-methylene)-(+)-camphorato] europium (III) derivative (5 Mg) to the CDCl$_3$ $^1$H NMR solution. The $^1$H NMR of this solution was then recorded and addition of the chiral shift reagent was continued until the singlet at δ 10.6 had split into two well-resolved peaks (ratio 7:1 ) for the crude material. A similar experiment was performed with the crystals of 9, and no splitting of the aldehyde peak was observed. Furthermore, X-ray diffraction analysis of these crystals showed the product was indeed a $C_2$ symmetric aromatic aldehyde. Therefore, the crystalline form of aldehyde 9 is of high enantiomeric purity. The 1 R-(+)-nopinone used to prepare aldehyde 9 $[α]^{25}D - +17$ (neat) was obtained from β-pinene $\{[α^{20}D=-21$ (neat, 92.1% ee)$\}$ (Brown, C. A.; Jadhav, P. K. *Org. Syn.* 1987, 65, 224, and which publication is incorporated heroin by reference in its entirety). Chiral shift experiments on this aldehyde failed to split the carbonyl proton. X-ray diffractional analysis of the crystalline styrene 11 and aldehyde 9 showed these materials to be $C_2$-symmetric.

EXAMPLE 10

Preparation of the $D_4$ Porphyrin 7.

Under an inert atmosphere the aldehyde 9 (0.54 g, 1.85 mmol) was dissolved in dichloromethane [123 mL (distilled over CaH$_2$)]. The reaction vessel was wrapped with aluminum foil and freshly distilled pyrrole (0.149 g, 0.155 mL, 2.22 mmol, 1.2 equivalent) was added. Anhydrous ethanol [(freshly distilled over magnesium/$I_2$) 0.5 mL] was then added (0.75% vol/vol). From a new bottle of boron trifluoride etherate (0.088 g, 0.76 mL, 0.62 mmol) was removed and dissolved in $CH_2Cl_2$ (2 mL). This solution was then added to the above mixture over 10 minutes. The formation of the porphyrinogen was followed by visible spectroscopy. An aliquot (0.05 cm$^3$) was added to p-chloranil (3 cm$^3$ of a 0.04-M solution in toluene), heated gently for 1 minute, 0.05 cm$^3$ of this solution was added to 3 cm$^3$ of ethanol/$CH_2Cl_2$ (1:1) and the intensity of the Soret band was noted. The intensity of the Soret band declined after 4 hours. At this point, p-chloranil (0.454 g, 1.85 mmol) was added and the resultant mixture was allowed to stir at 60° C. for one hour. The Soret band was monitored and further oxidant (0.114 g, 0.46 mmol, 2.31 mmol total) was added. After 2 hours, the reaction was allowed to cool to room temperature and 12 hours later, triethylamine (0.727 g, 1 mL, 7.71 mmol) was added, followed by Florosil® 100–200 mesh (1.5 g). This powder was packed onto a Florosil® column and eluted with pentane. The foremost fractions yielded the porphyrin as a purple glass-like powder (0.06 g, 9.7 % yield.)

$v_{max}$ 3314, and 2907 cm$^{-1}$; $^1$H NMR δ 8.5 (s, 8H, meso-Pyrrole H), 7.35 (s, 4H) 3.3 (m, 16H), 2.2 (t, J=2, 16H), 1.9 (t, J=3, 8H), 1.5 (t, J=5, 8H), 0.95 (s, 24H), 0.65 (s, 24H), and −2.59 (2H, br s, 2H); (FAB/CI) m/z 1368 (M$^+$+1, 17%) 1367 (M$^+$, 28), 1366 (33), and 1365 (17); Visible spectrum 402.1 (sh.), $\lambda_{max}$ 424, 520, 554, 614, and 666 nm. HRMS calculated for $C_{100}H_{110}N_4$ (FAB M$^+$) 1366.8731, found 1366.8742.

EXAMPLE 11

Metalation of the D4-symmetric porphyrin 7.

Under an inert atmosphere, the porphyrin 7 (30.5 mg, 22.7 μmol) was dissolved in benzene [5 mL (distilled over $CaH_2$)]/THF (5 mL) and to this mixture 2,6-lutidine (0.1 mL, 0.092 g, 0.85 mmol) was added. Anhydrous Mn(II)Br$_2$ (1 g, 4.6 mmol) was subsequently added, and the solution was then allowed to reflux for 6 hours. The solvent was then removed under reduced pressure and the residue was washed with 1% HCl (100 mL) for 10 minutes. The resultant chloromanganese (III) porphyrin was then extracted into $CH_2Cl_2$ (25 mL), the organic layer was then dried over $Na_2SO_4$, filtered, and the solvent was removed by rotary evaporation to give a green solid. The desired material was then extracted from this solid by column chromatography (silica/$CH_2Cl_2$/MeOH 50/50) to give a dark green resinous material (22.9 mg, 69%); $v_{max}$ 3354, and 2907 cm$^{-1}$; $\lambda_{max}$ 482 nm (log ε 4.75); (FAB/CI) m/z 1419 [m$^+$—Cl (100%)]; HRMS calculated for $C_{100}H_1108N_4Mn$ (FAB M$^+$) 1419.8080, found 1419.8037.

EXAMPLES 12–19

Epoxidation of Olefins using Chloromanganese porphyrin 7.

Epoxidations of olefins was carried out according to the method of Collman et al (Collman, J. P.; Kodadek, T. J.; Raybuck, S. A.; Meunier, B. *Proc. Natl. Acad. Sci. USA* 1983, 80, 7039, and which publication is incorporated herein by reference in its entirety). Porphyrin 7 (2 mg, 1.3 umol), 4'-(imidazol-1-yl)acetophenone (6.5 mg, 34 μmol), and benzyldimethyltetradecylammonium chloride (11 mg, 27 μmol) was dissolved in a standard solution of tridecane in $CH_2Cl_2$ [5 mL (4.1 mM)] and to this solution, styrene [freshly filtered through an alumina plug (25 μL, 22.7 mg, 219 μmol)] was added. This solution was then placed in an ice bath and allowed to cool to 0° C. An aliquot (10 μL) of this mixture was added to a solution of triphenyl phosphine in $CH_2Cl_2$ [1 mL, (76-mM)] and the initial absorbance ($\lambda_{482\ nm}$) was measured. A solution of lithium hypochlorite [(0.45-M) standardized by thiosulfate titration] was prepared as specified by Collman (Collman, J. P.; Brauman, J. I.; Meunier, B.; Hayashi, T.; Kodadek, T. J.; Raybuck, S. A, *J. Am. Chem. Soc.* 1985, 107, 2000, and which publication is incorporated herein by reference in its entirety), and 1.6 mL of this solution was then added to the reaction mixture. Vigorous stirring was then initiated and the reaction temperature was maintained at 0°–5° C. GLC [5 m capillary (internal diameter 0.53 mm), HP-1 (methyl silicone gum, 2.65 μm film thickness)] was used to monitor the progress of the reaction and the oxirane concentration was quantified against a standard solution of tridecane (4.1-mM) and styrene oxide (0.0135-M) in $CH_2Cl_2$. The olefin was consumed after 265 minutes, the final absorbance ($\lambda_{482\ nm}$) of the solution was then measured as stated earlier. The product was isolated as previously described in Collman, giving a red oil [0.018 g, yield 49% (adjusted by determination of the ratio of product to tridecane in the $^1$H NMR spectrum)]. The product was analyzed by chiral GLC using a Chiraldex G-TA capillary column (0.25 mm×20 m) (Advanced Separation Technologies, Inc., N.J.), the major enantiomer had the same retention time as a commercially available sample of 1R-(+) styrene oxide. The enantiomeric excess, 27%, was determined by $^1$H NMR experiments, using the chiral shift reagent Eu(hfc)$_3$ which was added in small aliquots (~5 mg) to the CDCl$_3$ solution of the product.

This method was used for the epoxidation of other substrates (see Table 1), and analysis was carried out as stated previously. The following exceptions were noted: 94 equivalent olefin was used for the epoxidation of cis phenyl propene and 1,2-dihydronaphthalene when using chloromanganese porphyrin 7. The isolated oxide from the epoxidation of cis phenyl propene with 7 had a number of side products that were unidentifiable. Decane (4.1-mM) was used as the internal standard for the epoxidation of 1,2-dihydronaphthalene and 2-vinylnaphthalene oxide. A Chiraldex G-TA capillary column (0.25 mm×20 m) (Advanced Separation Technologies, Inc., N.J.) was used to analyze the enantiomeric mixtures (see Table 1). The results of all these epoxidations are disclosed in Table 1.

TABLE 1

ASYMMETRIC EPOXIDATION REACTIONS.

| Example | Alkene | Catalyst | % Yield | % e.e. | Predominant Enantiomer | Rate (turnovers/hr) | % Catalyst Degradation |
|---|---|---|---|---|---|---|---|
| 12 | Styrene | Mn-7-Cl | 49 | 27[x] | 1R-(+) | 35 | 43 (121) |
| 13 | p-Methylstyrene | Mn-7-Cl | 65 | 21 | | 12 | 63 (141) |
| 14 | p-Chlorostyrene | Mu-7-Cl | 60 | 29 | | 14 | 51 (131) |
| 15 | Vinylnaphthalene | Mn-7-Cl | 89 | 22 | | 83 | 50 (146) |
| 16 | Indene | Mn-7-Cl | 56 | 18 | | 39 | 34 (117) |
| 17 | cis-phenylpropene | Mn-7-Cl | 34 | 28[x] | 1R,2S-(-) | 15 | 27 (56) |
| 18 | 1,2-Dihydro-naphthalene | Mn-7-Cl | 56 | 8 | | 46 | 24 (84) |
| 19 | 1-Phenyl-1-methylethene | Mn-7-Cl | 33 | 40[x] | 1S-(1) | 44 | 35 (68) |

α Catalyst degradation determined at total turnover number given in parenthesis.
[x]Prevalent enantiomer was determined by chiral GLC.

EXAMPLES 20–22

The procedure set forth in Example 12 was repeated three times using the alkenes listed in Table 2, but this time, the axial ligand employed was 1,5-dicyclohexyl imidazole (DCI) instead of [4'-(imidazol-1-yl)acetophenone] (IAP). The results of using another substituted imidazole is disclosed in Table 2.

TABLE 2

EPOXIDATION OF ALKENES USING CHLOROMANGANESE PORPHYRIN 7.

| Example | Alkene | Axial[d] Ligand | % Yield | % e.e. (G.C.) | Major Enantiomer | Rate (turnovers/hr) | Total Turnovers |
|---|---|---|---|---|---|---|---|
| 20 | Styrene | IAP | 49 | 27[c] | 1R-(+) | 35 | 121 |
|    |         | DCI | 77 | 68 | 1R-(+) | 48 | 135 |
| 21 | 4-Isobutylstyrene | DCI | — | 67 | (-)[b] | 355 | ~900 |
| 22 | 1-Phenyl-1-Methylene | IAP | 33 | 40[c] | 1S-(-)[b] | 44 | 68 |
|    |                      | DCI[a] | 95 | 67 | 1S-(-)[b] | 236 | 950 |

[a]Catalyst used was recycled from Examples 12 and 19 experiments for epoxidation of styrene and 4-isobutylstyrene.
[b]Major enantiomer was determined by qualitative optical polarimetry.
[c]Prevalent enantiomer was determined by $^1$H NMR.
[d]Axial ligands; DCI = 1,5-dicyclohexyl imidazole, IAP = 4'-(imidazol-1-yl)acetophenone.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A composition of matter which is:

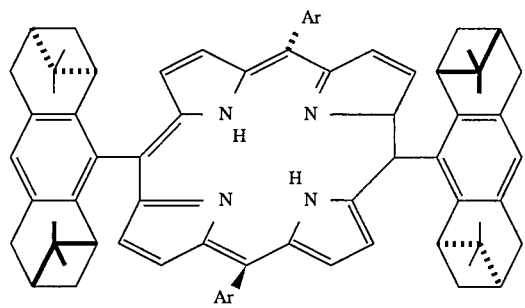

wherein Ar is the same arenyl group as shown on the left and right sides of the main structure.

2. A composition of matter which is:

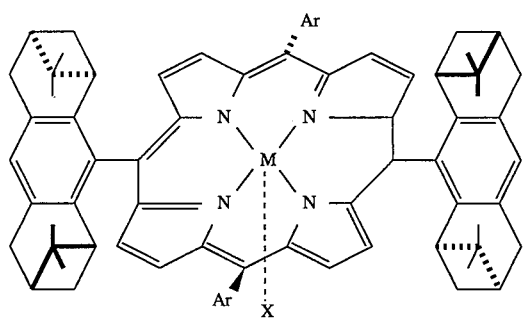

wherein M is selected from the group consisting of Mn, Fe, Al, Rh, Ni, Co, Ru, and Cu; Ar is the same arenyl group as shown on the right and left sides of the main structure; and X is counterion selected from the group consisting of Cl, Br, I, $BF_4$, and $PF_6$.

3. The composition as set forth in claim 2 wherein M is manganese.

4. The composition as set forth in claim 2 wherein M is iron.

5. The composition as set forth in claim 2 wherein M is aluminum.

6. The composition as set forth in claim 2 wherein M is rhodium.

7. The composition as set forth in claim 2 wherein M is nickel.

8. The composition as set forth in claim 2 wherein M is cobalt.

9. The composition as set forth in claim 2 wherein M is ruthenium.

10. The composition as set forth in claim 2 wherein M is copper.

11. The composition as set forth in claim 2 wherein there is also present, as an axial ligand, a substituted imidazole having the formula:

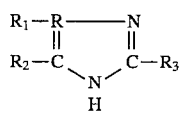

where $R_1$, $R_2$, and $R_3$ are equal or non-equal and are independently selected from the group consisting of H, alkyl $C_1$-$C_8$, cyclic alkyl, phenyl, and naphthyl.

12. The composition as set forth in claim 11 wherein the substituted imidazole is 1,5-dicyclohexyl imidazole.

13. The composition as set forth in claim 11 wherein the substituted imidazole is 4'-(imidazol-1-yl)acetophenone.

14. The composition as set forth in claim 12 wherein X is manganese.

15. The composition as set forth in claim 13 wherein X is manganese.

* * * * *